(12) United States Patent
Patt

(10) Patent No.: US 7,820,855 B2
(45) Date of Patent: Oct. 26, 2010

(54) METHOD AND APPARATUS FOR CARBONYLATING METHANOL WITH ACETIC ACID ENRICHED FLASH STREAM

(75) Inventor: Jeremy J. Patt, Lake Jackson, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 12/150,481

(22) Filed: Apr. 29, 2008

(65) Prior Publication Data

US 2009/0270650 A1 Oct. 29, 2009

(51) Int. Cl.
*C07C 51/12* (2006.01)
*C07C 53/08* (2006.01)

(52) U.S. Cl. ..................... 562/519; 562/607
(58) Field of Classification Search ............... None
See application file for complete search history.

(56) References Cited

U.S. PATENT DOCUMENTS

| | | | |
|---|---|---|---|
| 5,001,259 A | 3/1991 | Smith et al. ............ 562/519 |
| 5,026,908 A | 6/1991 | Smith et al. ............ 562/519 |
| 5,144,068 A | 9/1992 | Smith et al. ............ 562/519 |
| 5,416,237 A * | 5/1995 | Aubigne et al. ......... 562/519 |
| 5,696,284 A | 12/1997 | Baker et al. ............ 560/232 |
| 5,750,007 A | 5/1998 | Clode et al. ............. 203/3 |
| 5,770,768 A | 6/1998 | Denis et al. ............ 562/519 |
| 5,874,610 A * | 2/1999 | Clode et al. ............ 560/232 |
| 5,877,347 A | 3/1999 | Ditzel et al. ............ 562/519 |
| 5,877,348 A | 3/1999 | Ditzel et al. ............ 562/519 |
| 5,883,295 A | 3/1999 | Sunley et al. ............ 562/519 |
| 5,932,764 A | 8/1999 | Morris et al. ............ 562/519 |
| 5,942,460 A | 8/1999 | Garland et al. ........... 502/150 |

(Continued)

FOREIGN PATENT DOCUMENTS

CN  ZL92108244.4  4/1999

(Continued)

OTHER PUBLICATIONS

Research Report from 2006 Forum of the Southwest Research & Design Institute of Chemistry Industry (slides 1-32), entitled Process of 200ktpa Methanol Low Press Oxo Synthesis AA.

*Primary Examiner*—Karl J Puttlitz
(74) *Attorney, Agent, or Firm*—Michael W. Ferrell

(57) ABSTRACT

A carbonylation process for producing acetic acid including: (a) carbonylating methanol or its reactive derivatives in the presence of a Group VIII metal catalyst and methyl iodide promoter to produce a liquid reaction mixture including acetic acid, water, methyl acetate and methyl iodide; (b) feeding the liquid reaction mixture at a feed temperature to a flash vessel which is maintained at a reduced pressure; (c) heating the flash vessel while concurrently flashing the reaction mixture to produce a crude product vapor stream, wherein the reaction mixture is selected and the flow rate of the reaction mixture fed to the flash vessel as well as the amount of heat supplied to the flash vessel is controlled such that the temperature of the crude product vapor stream is maintained at a temperature less than 90° F. cooler than the feed temperature of the liquid reaction mixture to the flasher and the concentration of acetic acid in the crude product vapor stream is greater than 70% by weight of the crude product vapor stream.

14 Claims, 8 Drawing Sheets

U.S. PATENT DOCUMENTS

| | | | |
|---|---|---|---|
| 5,990,347 A | 11/1999 | Clode | 562/517 |
| 6,066,762 A | 5/2000 | Yoneda et al. | 562/519 |
| 6,114,576 A | 9/2000 | Leet et al. | 562/519 |
| 6,153,792 A | 11/2000 | Leet et al. | 562/519 |
| 6,627,770 B1 | 9/2003 | Cheung et al. | 562/519 |
| 6,657,078 B2 | 12/2003 | Scates et al. | 562/519 |

FOREIGN PATENT DOCUMENTS

| | | |
|---|---|---|
| EP | 0 759 419 A1 | 2/1997 |
| EP | 0 768 295 A1 | 4/1997 |
| EP | 0 849 248 A1 | 6/1998 |
| EP | 0 849 250 A1 | 6/1998 |
| GB | 2 112 394 A | 7/1983 |

\* cited by examiner

METHOD AND APPARATUS FOR CARBONYLATING METHANOL WITH ACETIC ACID ENRICHED FLASH STREAM

FIELD OF THE INVENTION

The present invention relates to acetic acid manufacture with improved efficiency provided by way of heating a flash vessel to maintain an elevated flash vapor temperature, generally more than 300° F. By way of the invention, the relative content of acetic acid in the crude product stream is increased, de-bottlenecking purification.

BACKGROUND

Acetic acid production by way of methanol carbonylation is well known in the art. Generally speaking, a methanol carbonylation production line includes a reactor, a flasher, purification and recycle. In the reactor section, methanol and carbon monoxide are contacted with rhodium or iridium catalyst in a homogenous stirred liquid phase reaction medium in a reactor to produce acetic acid. Methanol is pumped to the reactor from a methanol surge tank. The process is highly efficient, having a conversion of methanol to acetic acid of typically greater than 99 percent. A flash vessel coupled to the reactor flashes a draw stream in order to remove crude product from the reaction mixture. The crude product is fed to a purification section which includes generally a light ends or stripper column, a drying column, auxiliary purification and optionally a finishing column. In the process, various vent streams containing light ends, notably methyl iodide, carbon monoxide and methyl acetate are generated and fed to a light ends recovery section. These vent streams are scrubbed with a solvent to remove the light ends which are returned to the system or discarded.

It has been noted in various references that flash vessels used in carbonylation production processes may or may not be heated. See U.S. Pat. No. 5,874,610 to Clode et al. at Col. 2, lines 20-54; U.S. Pat. No. 5,750,007 to Clode et al. at Col. 2, lines 40-51; and U.S. Pat. No. 5,990,347 to Clode at Col. 2, lines 50-57. See also, U.S. Pat. No. 6,066,762 to Yoneda et al. which discloses a flash temperature of from 80° C.-180° C. (Col. 16, lines 40-44). It has not been appreciated, however, that temperature control within a relatively narrow window can be used to greatly increase the acetic acid content of the crude product stream in an acetic acid process. In conventional systems, flashing is typically carried out adiabatically and there is a large temperature drop relative to the feed stream because of the heat of vaporization of the crude product.

SUMMARY OF THE INVENTION

It has been unexpectedly determined in accordance with the present invention that moderate heat input to the flasher vessel can greatly increase the concentration of acetic acid in the crude product stream, reducing purification and recycle requirements. This finding is not intuitively apparent to one of skill in the art. Without intending to be bound by theory, it is believed that elevated flash temperatures vaporize more acetic acid and have little effect on the amount of light ends (methyl iodide, methyl acetate) that are flashed to the crude product vapor stream.

There is thus provided in one aspect of the invention a carbonylation process, for producing acetic acid comprising: (a) carbonylating methanol or its reactive derivatives in the presence of a Group VIII metal catalyst and methyl iodide promoter to produce a liquid reaction mixture including acetic acid, water, methyl acetate and methyl iodide; (b) feeding the liquid reaction mixture to a flash vessel which is maintained at a reduced pressure; (c) heating the flash vessel while concurrently flashing the reaction mixture to produce a crude product vapor stream, wherein the reaction mixture is selected and the flow rate of the reaction mixture to the flash vessel as well as the amount of heat supplied to the flash vessel is controlled such that the temperature of the crude product vapor stream is maintained at a temperature of greater than 300° F. and the concentration of acetic acid in the crude product vapor stream is greater than 70% by weight of the stream.

Further details and advantages will become apparent from the discussion which follows.

BRIEF DESCRIPTION OF DRAWINGS

The invention is described in detail below with reference to the drawings wherein like numerals designate similar parts. In the Figures.

DETAILED DESCRIPTION

Figure 1:
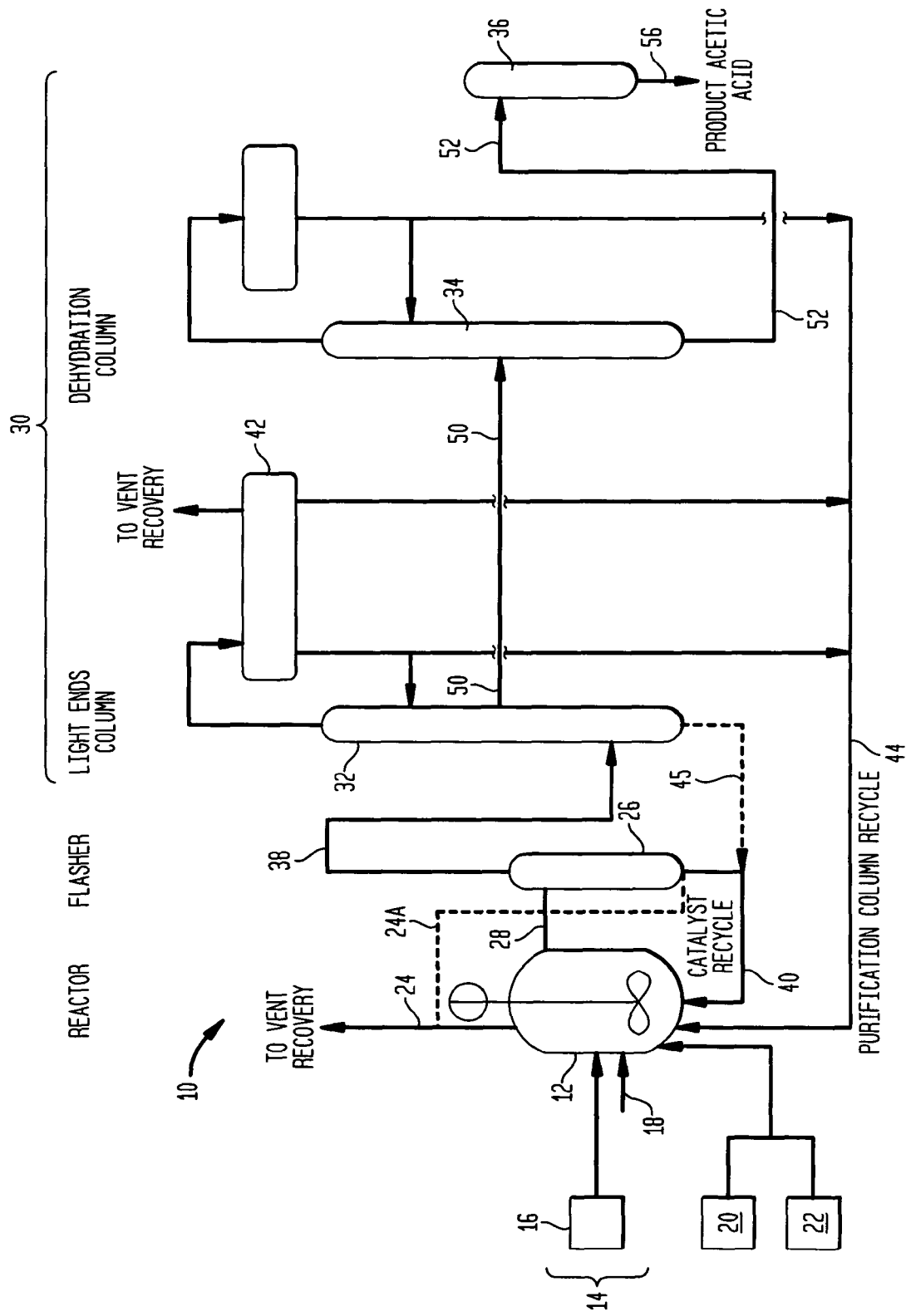
FIG. 1 is a schematic diagram showing a methanol carbonylation apparatus with purification.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. %, ppm and like terms refer to weight percent and parts per million by weight, unless otherwise indicated.

"Reduced pressure" refers to a pressure less than that of the reactor vessel.

A "like" stream undergoing flashing refers to a feed stream of the same composition which yields a product stream having the same flow rate of acetic acid in the flash vapor. See Tables 1-7.

The feed temperature of the reaction mixture to the flasher is measured as close as practical to the inlet of the flasher, on the high pressure side. Any suitable, instrumentation may be used.

The temperature of the crude product vapor stream is measured as close as practical to the vapor outlet of the flasher vessel.

A Group VIII catalyst metal used in connection with the present invention may be a rhodium and/or iridium catalyst.

The rhodium metal catalyst may be added in any suitable form such that rhodium is in the catalyst solution as an equilibrium mixture including $[Rh(CO)_2I_2]^-$ anion as is well known in the art. When rhodium solution is in the carbon monoxide-rich environment of the reactor, solubility of the rhodium is generally maintained because rhodium/carbonyl iodide anionic species are generally soluble in water and acetic acid. However, when transferred to carbon monoxide depleted environments as typically exist in the flasher, light ends column and so forth, the equilibrium rhodium/catalyst composition changes since less carbon monoxide is available. Rhodium precipitates as $RhI_3$, for example; details as to the form of entrained rhodium downstream of the reactor is not well understood. Iodide salts help alleviate precipitation in the flasher under so-called "low water" conditions as will be appreciated by one of skill in the art.

Iodide salts maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt or ligand that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide to generate the corresponding co-promoter iodide salt stabilizer. For additional detail regarding iodide salt generation, see U.S. Pat. Nos. 5,001,259 to Smith et al.; 5,026,908 to Smith et al.; and 5,144,068, also to Smith et al., the disclosures of which are hereby incorporated by reference. The iodide salt may be added as a phosphine oxide or any organic ligand, if so desired. These compounds and other ligands generally undergo quaternization in the presence of methyl iodide at elevated temperatures to yield suitable salts which maintain iodide anion concentration.

An iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2]^-H^+$, $Ir_4(CO)_{12}$, $IrCl_3 \cdot 3H_2O$, $IrBr_3 \cdot 3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in the following U.S. Pat. Nos. 5,942,460; 5,932,764; 5,883,295; 5,877,348; 5,877,347 and 5,696,284, the disclosures of which are hereby incorporated by reference into this application as if set forth in their entirety.

Methyl iodide is used as the promoter. Preferably, the concentration of methyl in the liquid reaction composition is in the range 1 to 50% by weight, preferably 2 to 30% by weight.

The promoter may be combined with a salt stabilizer/co-promoter compound, which may include salts of a metal of Group IA or Group IIA, or a quaternary ammonium or phosphonium salt. Particularly preferred are iodide or acetate salts, e.g., lithium iodide or lithium acetate.

Other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of [0.5 to 15]:1, preferably [2 to 10]:1, more preferably [2 to 7.5]:1. A suitable promoter concentration is 400 to 5000 ppm.

The present invention may be appreciated in connection with, for example, the carbonylation of methanol with carbon monoxide in a homogeneous catalytic reaction system comprising a reaction solvent (typically acetic acid), methanol and/or its reactive derivatives, a soluble rhodium catalyst, at least a finite concentration of water. The carbonylation reaction proceeds as methanol and carbon monoxide are continuously fed to the reactor. The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

The pressure of the carbonylation reaction is suitably in the range 10 to 200 Bar, preferably 10 to 100 bar, most preferably 15 to 50 Bar. The temperature of the carbonylation reaction is suitably in the range 100 to 300° C., preferably in the range 150 to 220° C. Acetic acid is typically manufactured in a liquid phase reaction at a temperature of from about 150-200° C. and a total pressure of from about 20 to about 50 bar.

Acetic acid is typically included in the reaction mixture as the solvent for the reaction.

Suitable reactive derivatives of methanol include methyl acetate, dimethyl ether, methyl formate and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 0.5 to 70% by weight, preferably 0.5 to 50% by weight, more preferably 1 to 35% by weight and most preferably 1-20% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range 0.1 to 16% by weight, more preferably 1 to 14% by weight, most preferably 1 to 10% by weight.

The reaction liquid is typically drawn from the reactor and flashed in a one step or multi-step process using a converter as well as a flash vessel as hereinafter described. The crude vapor process stream from the flasher is sent to a purification system which generally includes at least a light ends column and a dehydration column.

The present invention is further appreciated by reference to FIG. 1 which is a schematic diagram illustrating a typical carbonylation process and apparatus. In FIG. 1 there is shown a carbonylation system 10 including a reactor 12 provided with a feed system 14 including a methanol surge tank 16 and carbon monoxide feed line 18. A catalyst reservoir system includes a methyl iodide storage vessel 20 as well as a catalyst storage tank 22. Reactor 12 is provided with a vent 24 and an optional vent 24a. Reactor 12 is coupled to a flash vessel 26 by way of a conduit 28 and optionally by way of vent 24a. The flasher, in turn, is coupled to a purification section 30 which includes a light ends or stripper column 32, a dehydration column 34 and a strong acid, silver-exchanged cation ion-exchange resin bed 36 which removes iodides from the product. Instead of a silver-exchanged, strong acid cation ion-exchange resin, it has been reported that anion ion-exchange resin can be used to remove iodides. See British Patent No. G 2112394A, as well as U.S. Pat. No. 5,416,237, Col. 7, lines 54+, which teaches the use of 4-vinylpyridine resins for iodide removal.

A gaseous purge stream is typically vented from the head of the reactor to prevent buildup of gaseous by-products such as methane, carbon dioxide and hydrogen and to maintain a set carbon monoxide partial pressure at a given total reactor pressure. Optionally (as illustrated in Chinese Patent No. ZL92108244.4), a so-called "converter" reactor can be employed which is located between the reactor and flasher vessel shown in FIG. 1 and discussed further in connection with FIG. 2. Optionally, the gaseous purge streams may be vented through the flasher base liquid or lower part of the light ends column to enhance rhodium stability and/or they may be combined with other gaseous process vents (such as the purification column overhead receiver vents) prior to scrubbing. These variations are well within the scope of the present invention as will be appreciated from the appended claims and the description which follows.

As will be appreciated by one of skill in the art, the different chemical environments encountered in the purification train may require different metallurgy. For example, equipment at the outlet of the light ends column will likely require a zirconium vessel due to the corrosive nature of the process stream, while a vessel of stainless steel may be sufficient for equipment placed downstream of the dehydration column where conditions are much less corrosive.

Carbon monoxide and methanol are introduced continuously into reactor 12 with adequate mixing at a high carbon monoxide partial pressure. The non-condensable bi-products are vented from the reactor to maintain an optimum carbon monoxide partial pressure. The reactor off gas is treated to recover reactor condensables, i.e., methyl iodide before flaring. Methanol and carbon monoxide efficiencies are generally greater than about 98 and 90% respectively. As will be appreciated from the Smith et al. patent noted above, major inefficiencies of the process are the concurrent manufacture of carbon dioxide and hydrogen by way of the water gas shift reaction.

From the reactor, a stream of the reaction mixture is continuously fed via conduit 28 to flasher 26. Through the flasher the product acetic acid and the majority of the light ends (methyl iodide, methyl acetate, and water) are separated from the reactor catalyst solution, and the crude process stream 38 is forwarded with dissolved gases to the distillation or purification section 30 in single stage flash. The catalyst solution is recycled to the reactor via conduit 40. In accordance with the invention, the flasher is heated with steam, for example, by way of jacketing or coils in order to raise the temperature of stream 38. Alternative heating means such as electric heating or radiant (microwave) heating can be used if more convenient.

The purification of the acetic acid typically includes distillation in a light ends column, a dehydration column, and, optionally, a heavy ends column. The crude vapor process stream 38 from the flasher is fed into the light ends column 32. Methyl iodide, methyl acetate, and a portion of the water condense overhead in the light end columns to form two phases (organic and aqueous) in a receiver 42. Both overhead liquid phases return to the reaction section via recycle line 44. Optionally, a liquid recycle stream 45 from the light ends column may also be returned to the reactor.

The purified process stream 50 is drawn off the side of the light ends column 32 and is fed into dehydration column 34. Water and some acetic acid from this column separate and are recycled to the reaction system via recycle line 44 as shown. The purified and dried process stream 52 from the dehydration column 34 feeds resin bed 36 and product is taken therefrom at 56 as shown. Carbonylation system 10 uses only two primary purification columns and is preferably operated as described in more detail in U.S. Pat. No. 6,657,078 to Scates et al., entitled "Low Energy Carbonylation Process", the disclosure of which is incorporated herein by reference. Additional columns are generally used as desired, depending on the system.

Figure 2:
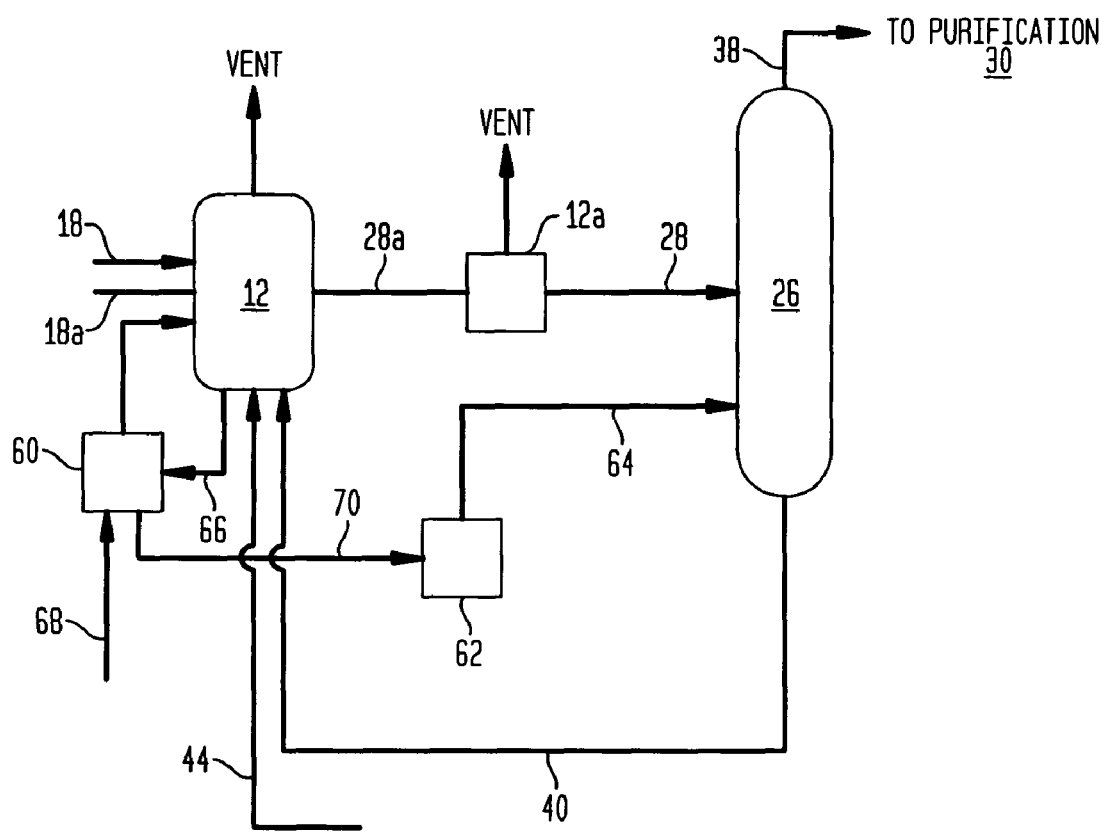
FIG. 2 is a schematic diagram showing an alternate layout of the reactor and flasher vessels wherein there is provided a heat exchanger for providing heat from the reactor to the flasher and a converter vessel between the reactor and flasher.

There is shown in FIG. 2 an alternate layout of the reactor/flasher with a converter vessel 12a therebetween as well as a heat exchanger 60 and a low pressure steam flash vessel 62. Reactor 12 and flasher 26 operate as described above. Methanol and carbon monoxide are provided to reactor 12 at 18a, 18 and liquid reaction mixture is drawn at 28a and provided to converter vessel 12a which vents gas including light ends to a scrubber (not shown). The vent gas can be scrubbed with methanol and returned to the reactor. Converter 12a feeds flasher 26 where the pressure is reduced and flashed to crude product stream 38. Recycle to the reactor is provided by way of lines 40, 44 as is discussed above in connection with FIG. 1.

Flasher 26 is heated by way of a low pressure steam supply 64 provided from a steam flash vessel 62 which is fed from heat exchanger 60. Heat exchanger 64 is made with suitable metallurgy and receives hot catalytic mixture from reactor 12 via line 66 as well as steam condensate via line 68. The condensate is heated by the hot catalyst which, in turn, requires cooling because of the exothermic nature of the carbonylation reaction. The heated condensate is supplied to vessel 62 via line 70 where it is flashed to (low pressure) steam and used to heat flasher 26 as noted above.

Thus, heat exchanger 64 as shown in FIG. 2 provides cooling to the reactor and heat to the flasher which reduces overall energy costs as will be appreciated by one of skill in the art.

Carbon monoxide may be added directly to converter 12a if so desired or may be added slightly before (upstream) or after (downstream) if so desired in order to stabilize the catalyst solution and consume any unreacted methanol.

Details of such arrangements are seen in European Patent No. EP 0 759 419 as well as U.S. Pat. No. 5,770,768 to Denis et al., the disclosures of which are hereby incorporated by reference.

Whether or not heat transfer from the reactor to the flasher is employed, the present invention substantially increases the efficiency of the system by providing a higher concentration of acetic acid in the crude product vapor stream as will be appreciated form the discussion which follows.

Figure 3:
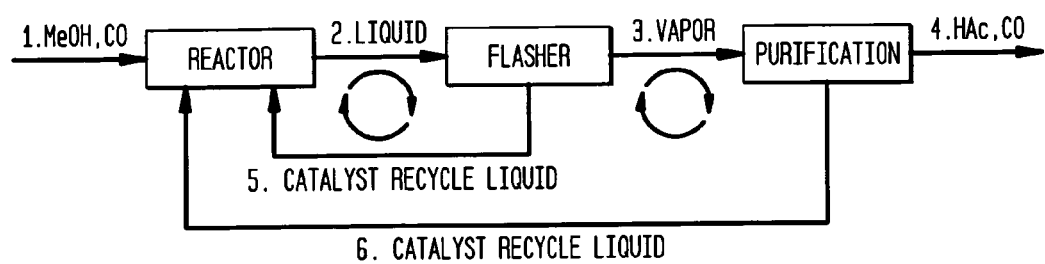
FIG. 3 is a flow chart schematically illustrating operation of the apparatus of FIGS. 1 and 2.

The carbonylation apparatus shown in FIG. 1 and that illustrated in FIG. 2 can be represented schematically as shown in FIG. 3 for present purposes. In FIG. 3, the feed to the reactor is designated stream 1, the liquid stream to the flasher is designated stream 2, the crude product vapor stream provided to the splitter column is designated stream 3 and the purified product stream is labeled stream 4. Stream 5 represents the catalyst recycle stream from the flasher and stream 6 represents recycle from purification recycle to the reactor.

FIG. 3 illustrates two major inefficiencies of the methanol carbonylation process generally; catalyst recycle (5) and purification recycle (6). Both of these internal 'flywheels' are energy and capital-intensive and could be minimized by improving performance of the flasher—by ensuring that the vapor stream that it sends to purification (3) has proportionally more HAc and less "non-product" components ($H_2O$, MeAc, MeI). This can be accomplished by providing heat input to raise the operating temperature of the flasher. The benefits of this concept are illustrated in the following examples.

A semi-empirical simulator was used to study the effect of flash temperature while holding constant the mass flow of HAc in the vapor stream (3). The stream compositions are shown below for vapor (3) and liquid (5) exiting the flasher. The flasher inlet basis is a stream at 387° P, 400 psig, containing 8.1 wt % MeI, 2.9 wt % MeAc, 75.7 wt % HAc, 2.8 wt % $H_2O$, and 10.6 wt % LiI. Flash temperature (temperature of the vapor stream) was varied from adiabatic (297° F.) to isothermal (387° F.), all cases to 25 psig.

Results appear in Tables 1-7 and FIGS. 4-7.

TABLE 1

Comparative Example A - Adiabatic Operation of Flasher

|  | INLET | VAPOR | LIQUID |
|---|---|---|---|
| T (F.) | 387 | 297 | 297 |
| Flow |  |  |  |
| Total | 1554.42 | 260.37 | 1294.05 |
| Total-HAc |  | 89.48 |  |
| MeI | 125.17 | 58.31 | 66.86 |
| MeAc | 45.18 | 20.42 | 24.76 |
| HAc | 1175.98 | 170.89 | 1005.09 |
| $H_2O$ | 43.81 | 10.76 | 33.05 |
| LiI | 164.29 | 0.00 | 164.29 |
| Weight % |  |  |  |
| MeI | 8.1 | 22.4 | 5.2 |
| MeAc | 2.9 | 7.8 | 1.9 |
| HAc | 75.7 | 65.6 | 77.7 |
| $H_2O$ | 2.8 | 4.1 | 2.6 |
| LiI | 10.6 | 0.0 | 12.7 |

TABLE 2

Example 1 - Operation of Flasher Maintaining Vapor at 300° F.

|  | INLET | VAPOR | LIQUID |
|---|---|---|---|
| T (F.) | 387 | 300 | 300 |
| Flow |  |  |  |
| Total | 878.28 | 241.52 | 636.76 |
| Total-HAc |  | 70.63 |  |
| MeI | 70.72 | 44.96 | 25.76 |
| MeAc | 25.53 | 15.82 | 9.70 |
| HAc | 664.45 | 170.89 | 493.56 |
| $H_2O$ | 24.75 | 9.84 | 14.91 |
| LiI | 92.82 | 0.00 | 92.82 |
| Weight % |  |  |  |
| MeI | 8.1 | 18.6 | 4.0 |
| MeAc | 2.9 | 6.6 | 1.5 |
| HAc | 75.7 | 70.8 | 77.5 |
| $H_2O$ | 2.8 | 4.1 | 2.3 |
| LiI | 10.6 | 0.0 | 14.6 |

TABLE 3

Example 2 - Operation of Flasher Maintaining Vapor at 305° F.

|  | INLET | VAPOR | LIQUID |
|---|---|---|---|
| T (F.) | 387 | 305 | 305 |
| Flow |  |  |  |
| Total | 480.70 | 222.04 | 258.66 |
| Total-HAc |  | 51.15 |  |
| MeI | 38.71 | 31.48 | 7.23 |
| MeAc | 13.97 | 11.17 | 2.80 |
| HAc | 363.67 | 170.89 | 192.78 |
| $H_2O$ | 13.55 | 8.50 | 5.04 |
| LiI | 50.80 | 0.00 | 50.80 |
| Weight % |  |  |  |
| MeI | 8.1 | 14.2 | 2.8 |
| MeAc | 2.9 | 5.0 | 1.1 |
| HAc | 75.7 | 77.0 | 74.5 |
| $H_2O$ | 2.8 | 3.8 | 1.9 |
| LiI | 10.6 | 0.0 | 19.6 |

TABLE 4

Example 3 - Operation of Flasher Maintaining Vapor at 310° F.

|  | INLET | VAPOR | LIQUID |
|---|---|---|---|
| T (F.) | 387 | 310 | 310 |
| Flow |  |  |  |
| Total | 351.38 | 212.96 | 138.42 |
| Total-HAc |  | 42.07 |  |
| MeI | 28.29 | 25.35 | 2.94 |
| MeAc | 10.21 | 9.05 | 1.16 |
| HAc | 265.83 | 170.89 | 94.94 |
| $H_2O$ | 9.90 | 7.67 | 2.24 |
| LiI | 37.14 | 0.00 | 37.14 |
| Weight % |  |  |  |
| MeI | 8.1 | 11.9 | 2.1 |
| MeAc | 2.9 | 4.2 | 0.8 |
| HAc | 75.7 | 80.2 | 68.6 |
| $H_2O$ | 2.8 | 3.6 | 1.6 |
| LiI | 10.6 | 0.0 | 26.8 |

TABLE 5

Example 4 -
Operation of Flasher Maintaining Vapor at 325° F.

|  | INLET | VAPOR | LIQUID |
|---|---|---|---|
| T (F.) | 387 | 325 | 325 |
| Flow |  |  |  |
| Total | 265.59 | 205.71 | 59.88 |
| Total-HAc |  | 34.82 |  |
| MeI | 21.39 | 20.58 | 0.81 |
| MeAc | 7.72 | 7.39 | 0.33 |
| HAc | 200.93 | 170.89 | 30.04 |
| $H_2O$ | 7.49 | 6.86 | 0.63 |
| LiI | 28.07 | 0.00 | 28.07 |
| Weight % |  |  |  |
| MeI | 8.1 | 10.0 | 1.4 |
| MeAc | 2.9 | 3.6 | 0.6 |
| HAc | 75.7 | 83.1 | 50.2 |
| $H_2O$ | 2.8 | 3.3 | 1.0 |
| LiI | 10.6 | 0.0 | 46.9 |

TABLE 6

Example 5 -
Operation of Flasher Maintaining Vapor at 350° F.

|  | INLET | VAPOR | LIQUID |
|---|---|---|---|
| T (F3) | 387 | 350 | 350 |
| Flow |  |  |  |
| Total | 241.97 | 203.50 | 38.47 |
| Total-HAc |  | 32.61 |  |
| MeI | 19.48 | 19.14 | 0.34 |
| MeAc | 7.03 | 6.89 | 0.14 |
| HAc | 183.06 | 170.89 | 12.17 |
| $H_2O$ | 6.82 | 6.58 | 0.24 |
| LiI | 25.57 | 0.00 | 25.57 |
| Weight % |  |  |  |
| MeI | 8.1 | 9.4 | 0.9 |
| MeAc | 2.9 | 3.4 | 0.4 |
| HAc | 75.7 | 84.0 | 31.6 |
| $H_2O$ | 2.8 | 3.2 | 0.6 |
| LiI | 10.6 | 0.0 | 66.5 |

TABLE 7

Example 6 -
Isothermal Operational Flasher

|  | INLET | VAPOR | LIQUID |
|---|---|---|---|
| T (F.) | 387 | 387 | 387 |
| Flow |  |  |  |
| Total | 233.35 | 202.68 | 30.67 |
| Total-HAc |  | 31.79 |  |
| MeI | 18.79 | 18.61 | 0.18 |
| MeAc | 6.78 | 6.71 | 0.08 |
| HAc | 176.54 | 170.89 | 5.64 |
| $H_2O$ | 6.58 | 6.47 | 0.11 |
| LiI | 24.66 | 0.00 | 24.66 |
| Weight % |  |  |  |
| MeI | 8.1 | 9.2 | 0.6 |
| MeAc | 2.9 | 3.3 | 0.2 |
| HAc | 75.7 | 84.3 | 18.4 |
| $H_2O$ | 2.8 | 3.2 | 0.3 |
| LiI | 10.6 | 0.0 | 80.4 |

Figure 4:
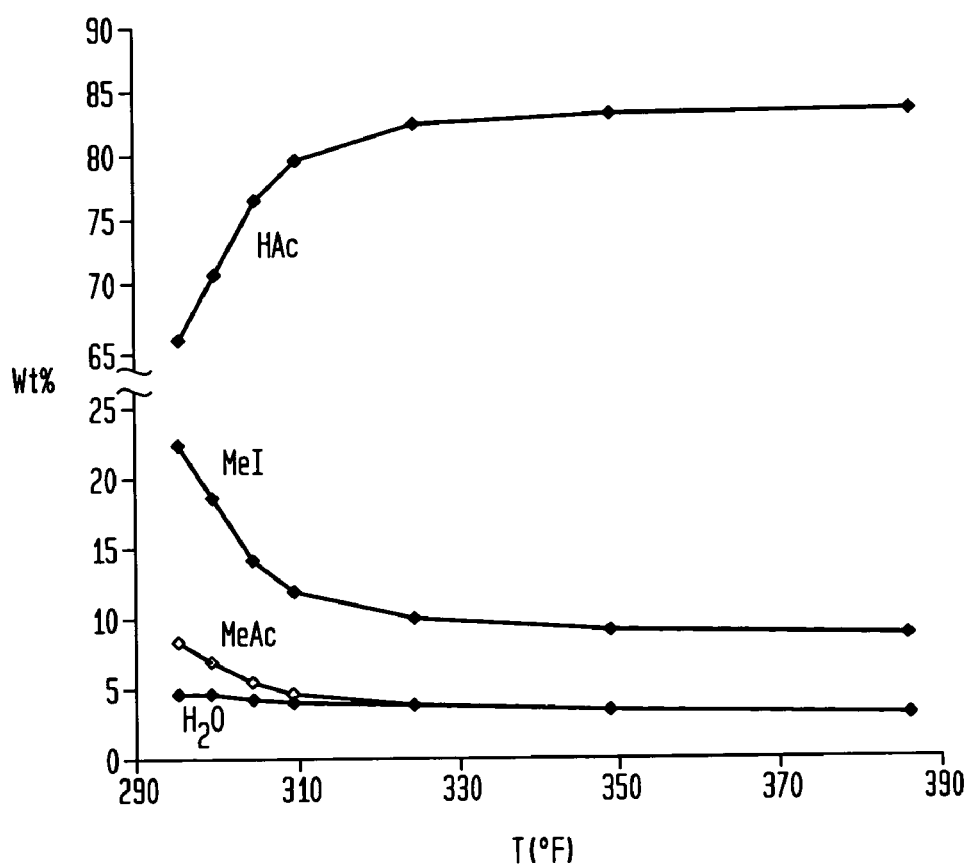
FIG. 4 is a graph showing crude product vapor concentration as a function of flasher temperature.
Figure 5:
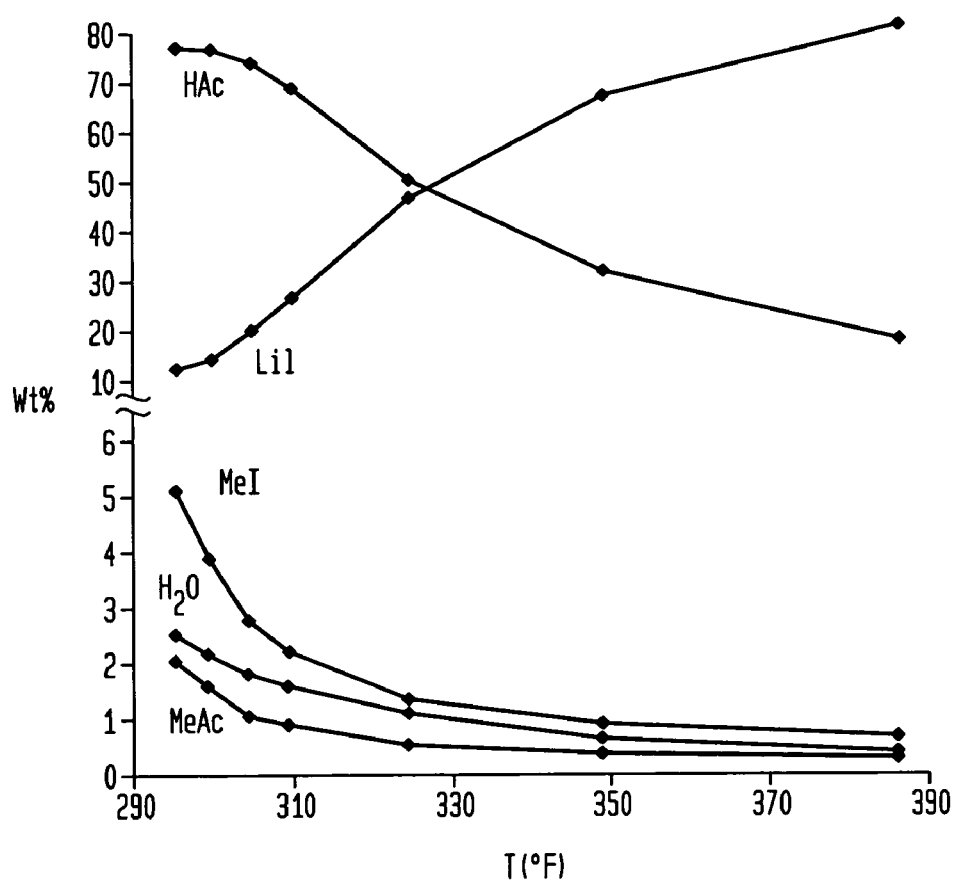
FIG. 5 is a plot illustrating composition of the flash liquid vs. flasher temperature.

As shown in the data and on FIG. 4, increasing the flasher temperature increases the HAc wt % in the vapor stream (3) while decreasing concentrations of all other components. FIG. 5 illustrates that the proportion of LiI in the catalyst recycle stream (5) increases with increasing flash temperature. This high LiI acts to improve catalyst stability in the flasher (possibly compensating for any detrimental effects of higher operating temperature).

Figure 6:
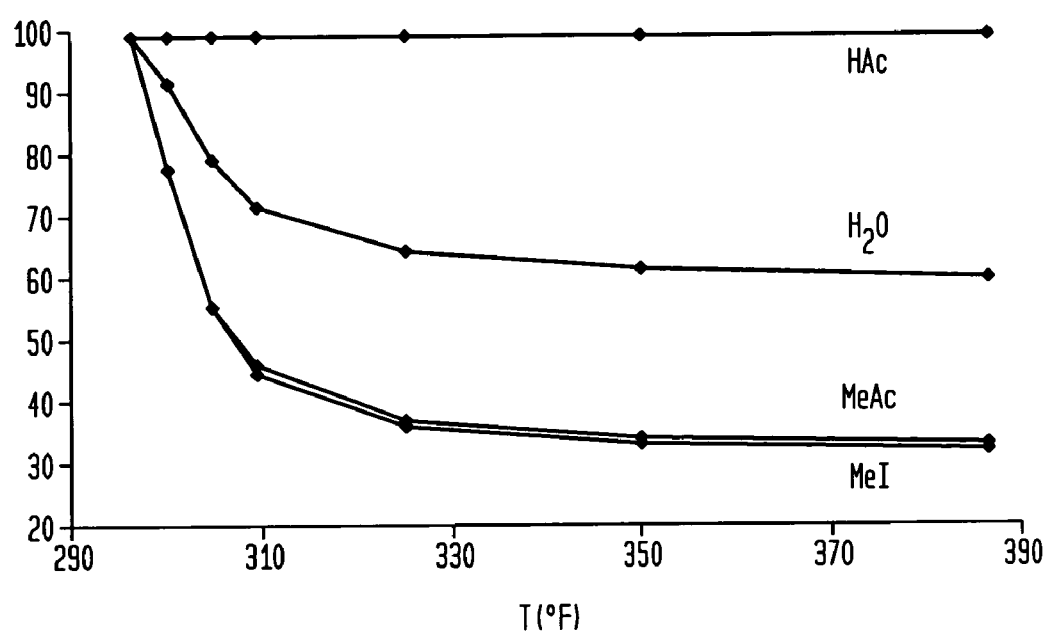
FIG. 6 is a plot of normalized mass flow rate of the various components in the flash vapor vs. flash temperature.

FIG. 6 shows the effect of flasher temperature on the mass flow rate of each component in the vapor stream that is fed to purification (3). It shows that for a set amount of HAc throughput, smaller quantities of the "non-product" components are sent to purification when using a higher flash temperature. For example, raising the flash temperature from 297 to 310° F. would decrease the mass flow of water sent to purification by 30%, MeAc by 55% and MeI by 55%.

Figure 7:
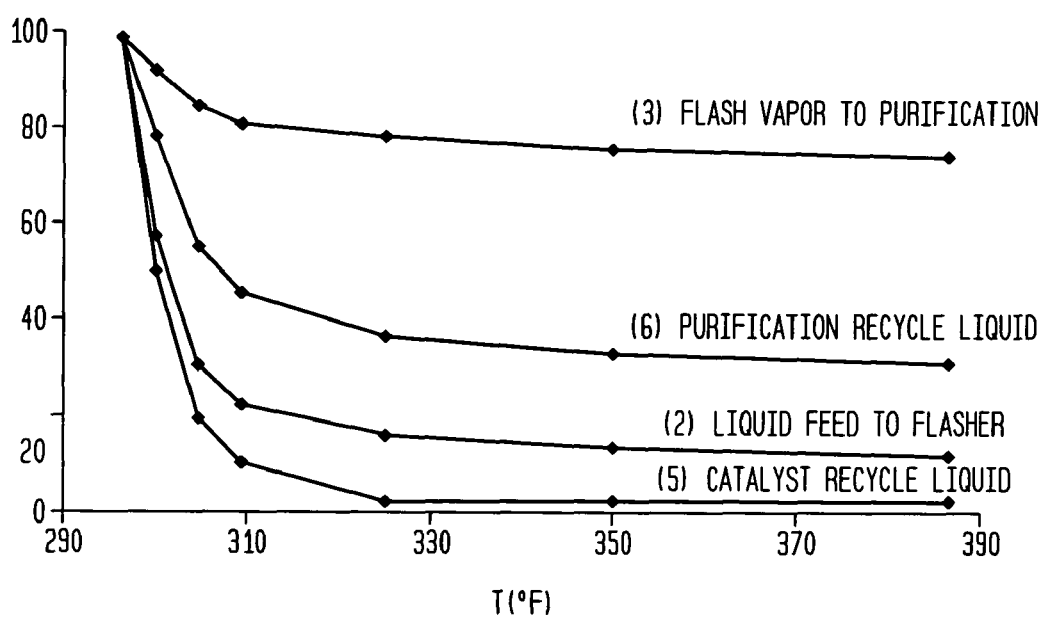
FIG. 7 is a plot of mass flow rates of various streams vs. flash temperature.

It is seen in FIG. 7 that the flow rate requirements of the streams are significantly lower when operating the flasher at a higher temperature. This is a result of proportionally more HAc in the vapor stream exiting the flasher (3) and less of the "non-product" components. A lower flow rate of flasher feed (2) is required to attain the same mass throughput of HAc to purification (3). For example, by raising flash temperature from 297 to 310° F., the required catalyst recycle rate drops by 90%, liquid feed to flasher by 80%, purification recycle by 50% and vapor feed to purification by 20%. Benefits include: (1) for an existing unit, increasing HAc in the crude product stream, thus debottlenecking purification and lower operating costs and/or allow an increase in capacity; (2) running the reactor at higher MeAc, currently this level is typically constrained by purification capacity, higher MeAc also allows the reactor to operate at a lower temperature and also decreases the make rate of propionic acid; (3) for a new unit, the capital and energy requirements are reduced by requiring less catalyst recycle and purification throughput for a given production rate of HAc; (4) decrease in vapor feed rate to purification reduces catalyst loss via entrainment; and (5) decrease in liquid feed rate to the flasher improves CO efficiency by significantly reducing the carryover loss of soluble CO (which currently accounts for 80% of the total CO waste).

For example, increasing flasher operating temperature from 297 to 310° decreases the required flowrate to the flasher by 80%. This modification decreases the total CO inefficiency dramatically, by ~60% (=80% reduction of the 80% of CO loss from flasher carryover).

Figure 8:
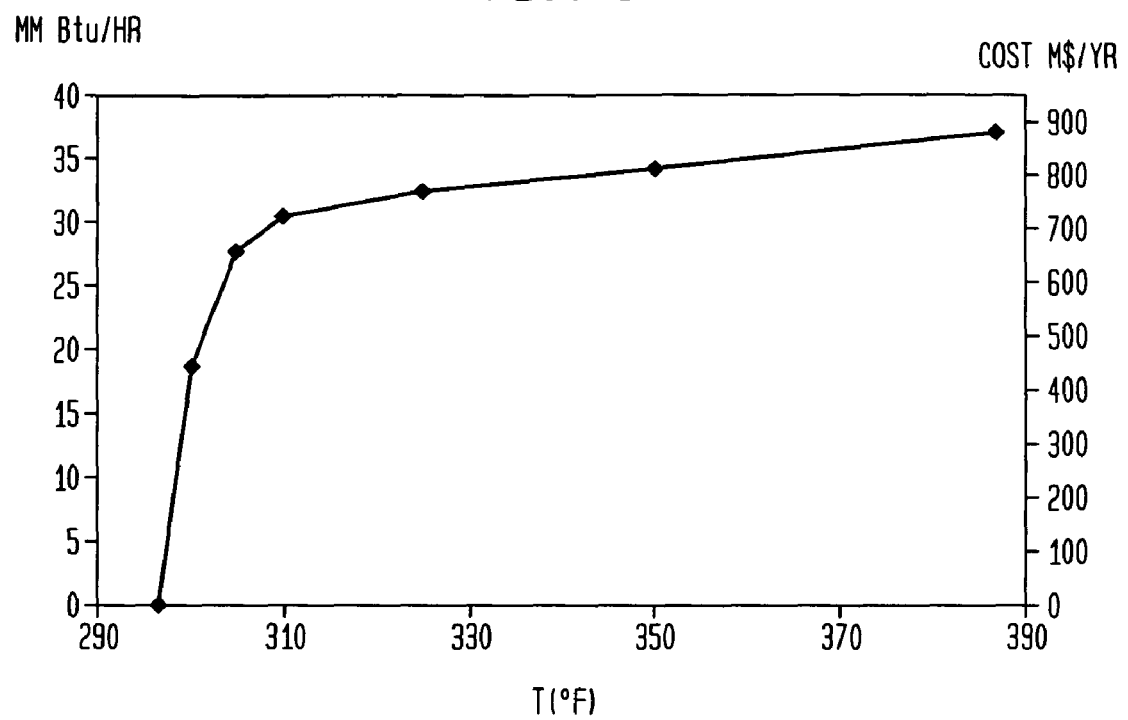
FIG. 8 is a plot illustrating heated flasher energy consumption and cost vs. temperature.

The energy cost of heating the flasher with steam is shown in FIG. 8. This cost would be significantly reduced by integrating heat between the reactor and flasher as is shown in FIG. 2. For example, to heat to 310° F., it is possible to use the reactor cooling loop to heat the flasher.

While the invention has been illustrated in connection with particular equipment and operating conditions, modifications to these examples within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary.

What is claimed is:

1. A carbonylation process for producing acetic acid comprising:
(a) carbonylating methanol or its reactive derivatives in the presence of a rhodium metal catalyst and methyl iodide promoter to produce a liquid reaction mixture including acetic acid, water, methyl acetate and methyl iodide;

(b) feeding the liquid reaction mixture to a flash vessel which is maintained at a reduced pressure;

(c) heating the flash vessel while concurrently flashing the reaction mixture to produce a crude product vapor stream, wherein the reaction mixture is selected and the flow rate of the reaction mixture to the flash vessel as well as the amount of heat supplied to the flash vessel is controlled such that the temperature of the crude product vapor stream is maintained at a temperature of greater than 300° F., as measured as close as practical to a vapor outlet of the flash vessel, and the concentration of acetic acid in the crude product vapor stream is greater than 70% by weight of the stream.

2. The carbonylation process according to claim 1, wherein the temperature of the crude product vapor stream is maintained at a temperature of greater than 300° F. and less than 400° F.

3. The carbonylation process according to claim 1, wherein the temperature of the crude product vapor stream is maintained at a temperature of greater than 300° F. and less than 350° F.

4. The carbonylation process according to claim 1, wherein the amount of water in the reaction mixture is maintained at a level of from 1% by weight to 10% by weight of the reaction mixture and the reaction mixture further comprises an iodide salt co-promoter.

5. The carbonylation process according to claim 4, wherein the iodide salt co-promoter is present in an amount that generates an iodide anion concentration of from about 4 weight % to about 20 weight % of the reaction mixture.

6. The carbonylation process according to claim 4, wherein the iodide salt co-promoter is a mixture of iodide salts.

7. The carbonylation process according to claim 4, wherein the iodide salt co-promoter is provided to the reaction mixture in the form of an iodide ligand precurser.

8. The carbonylation process according to claim 5, wherein the amount of water in the reaction mixture is maintained at a level of from 1% by weight to 5% by weight of the reaction mixture.

9. The carbonylation process according to claim 1, wherein the rhodium metal catalyst is present in the reaction mixture at a concentration of from about 300 ppm to about 5,000 ppm by weight of the reaction mixture.

10. The carbonylation process according to claim 1, wherein carbonylation is carried out under a gauge pressure of from 10 to 100 bar.

11. The carbonylation process according to claim 1, wherein the flash vessel is maintained at a gauge pressure of from about 0.25 to about 3 bar.

12. The carbonylation process according to claim 1, wherein the crude product vapor stream is maintained at a temperature of about 325° F. or greater.

13. The carbonylation process according to claim 1, wherein the concentration of methyl iodide in the crude product vapor stream is less than about 20% by weight of the stream.

14. The carbonylation process according to claim 1, wherein more than about 25 weight % of acetic acid in the reaction mixture introduced to the flash vessel is flashed to the crude product vapor stream.

* * * * *